United States Patent [19]

Gilbert et al.

[11] Patent Number: 4,969,883
[45] Date of Patent: Nov. 13, 1990

[54] MEDICAMENT VIAL END CAP MEMBRANE PIERCING DEVICE

[76] Inventors: Michael D. Gilbert, 5845 Canyon View Dr.; Lonnie R. Mabley, 6181 Woodbrook Cir.; Dennis V. Worthington, 2020 Picnic La., all of Paradise, Calif. 95969

[21] Appl. No.: 293,094

[22] Filed: Jan. 3, 1989

[51] Int. Cl.⁵ .............................................. A61B 19/00
[52] U.S. Cl. ...................................... 604/414; 604/88; 604/192; 604/905; 215/DIG. 3
[58] Field of Search ...................................... 604/86–88, 604/192, 201–203, 263, 408, 411–414, 905; 215/DIG. 3

[56] References Cited

U.S. PATENT DOCUMENTS

| | | | |
|---|---|---|---|
| 2,816,550 | 12/1957 | Hudson | 604/413 |
| 3,826,261 | 7/1974 | Killinger | 604/414 X |
| 3,976,073 | 8/1976 | Quick et al. | 604/414 |
| 4,059,112 | 11/1977 | Tischlinger | 604/413 |
| 4,116,196 | 9/1978 | Kaplan et al. | 604/192 |
| 4,232,669 | 11/1980 | Nitshke | 604/192 |
| 4,601,704 | 7/1986 | Larkin | 604/88 X |
| 4,752,292 | 6/1988 | Lopez et al. | 604/244 |
| 4,834,716 | 5/1989 | Ogle, II | 604/192 |

Primary Examiner—C. Fred Rosenbaum
Assistant Examiner—C. Maglione
Attorney, Agent, or Firm—Mark C. Jacobs

[57] ABSTRACT

A spear-like device for puncturing the membrane or diaphragm stopper of a liquid medicament vial. The spear-like device includes a fluid supply port from which liquid can be delivered to a hooded needle.

4 Claims, 2 Drawing Sheets

MEDICAMENT VIAL END CAP MEMBRANE PIERCING DEVICE

FIELD OF THE INVENTION

This invention relates generally, to hypodermic syringes for withdrawing, transporting and injecting liquid medicines and other fluids, and more particularly, to an improved apparatus for accomplishing such fluid transfer without fear of contact between the hypodermic needle and using personnel, either during insertion and assembly of the components or as they are being withdrawn and disassembled.

BACKGROUND OF THE INVENTION

Intravenous fluid dispensing bags are provided with a fluid supply port, into which the needle of a hypodermic syringe can be introduced and through which fluid medicines are injected into the bag for dispensing to the patient intravenously. The process of withdrawing medicine from a vial into a hypodermic syringe, transporting it safely without contamination and injecting it into an intravenous fluid dispensing bag has been the subject of much prior art devoted to preventing needle breakage and preventing needle contamination from the environment to which the syringe is exposed. Protective sheaths and hoods encircling the needle are well-known, as are removable protective covers and needle guides, all intended to relieve these problems.

However, the increase in incurable infectious diseases has raised new concerns for the safety of people who use hypodermic syringes, particularly from accidental needle pricks which penetrate the skin. The prior art does not address this problem, at least as far as disclosing apparatus and methods which make accidental needle punctures essentially impossible. It will be acknowledged that the wearing of surgical gloves by attending personnel is a reliable first line of defense with regards to spilled fluids but such a precaution offers no protection against needle pricks wherein either the needle or fluid carried thereby have become contaminated.

Liquid medicine to be given to patients intravenously are supplied from the drug manufacturers in vials or bottles having a rubber stopper seal held in place by a crimped band of aluminum or other metal. To transfer medicament from this vial a hypodermic syringe needle is inserted through the rubbber stopper, perforating it and entering the vial. The medicament is drawn off into the syringe until the syringe holds the required measured amount. The needle is then withdrawn from the vial and inserted into the fluid supply port of an intravenous fluid dispensing bag containing the carrier fluid to be dispensed intravenously. The medicine injected into the bag's fluid contents is mixed therewith and is then ready for administering to the patient.

This process, which involves handling the syringe frequently, makes needle breakage and skin pricks a recurring problem. Transporting the syringe after filling and before injection can also create opportunities for the needle to be exposed to the environment for extended periods. Much of the prior art discloses devices which attempt to relieve these problems, generally by sheathing the needle and providing it with a protective cover both for guiding the needle over a medicament port and for protecting the withdrawn solution from contamination.

U.S. Pat. No. 3,826,261 to Killinger discloses a syringe with the needle surrounded by a cylindrical sheath, adapted for communication with a tubular conduit comprising part of a sealed cap which closes the neck of a medicament vial and seals it.

U.S. Pat. No. 4,128,098 issued to Bloom et al discloses a valved spike for insertion into the rubber stopper of a sealed medicament vial, and requires only one puncture of the stopper instead of the repeated punctures from syringe needles normally encountered when syringes are filled repeatedly from the same vial.

U.S. Pat. No. 4,232,669 to Nitshke discloses a syringe for use with flexible bags, the syringe having a cylindrical sheath surrounding the needle portion and serving to guide and support the needle. This patent also discloses a cap for the sheath to protect the needle for use.

However, none of this prior art is devoted to means for preventing human contact with the sharpened needle during all the steps in transforming medicament from vials to IV plastic bags, nor is the connection between the syringe, vials and IV bags necessarily the same.

SUMMARY OF THE INVENTION

An object is to provide a piercing spear device to puncture the flat diaphragm stopper on a liquid medicine vial, penetrate it and by projecting barb means prevent withdrawal, with the spear device having a fluid supply port for mating engagement with a hooded needle.

Another still further object is to provide a kit for transferring liquid medicine comprising a hooded needle and hypodermic syringe with a concentric end cap to cover and seal the recessed needle, a fluid supply port and stopper for maintaining by standard means a medicine vial, and a piercing spear device and fluid supply port for piercingly mounting on a standard flattop medicine vial.

Another object is to provide a method for manufacturing the apparatus of this invention.

A further object is to provide a method for assembling the medical fluid dispensing apparatus of this invention.

BRIEF DESCRIPTION OF THE DRAWINGS

Similar reference characters designate corresponding parts throughout the several views of the drawings.

DESCRIPTIN OF THE PREFERRED EMBODIMENT

Figure 1:
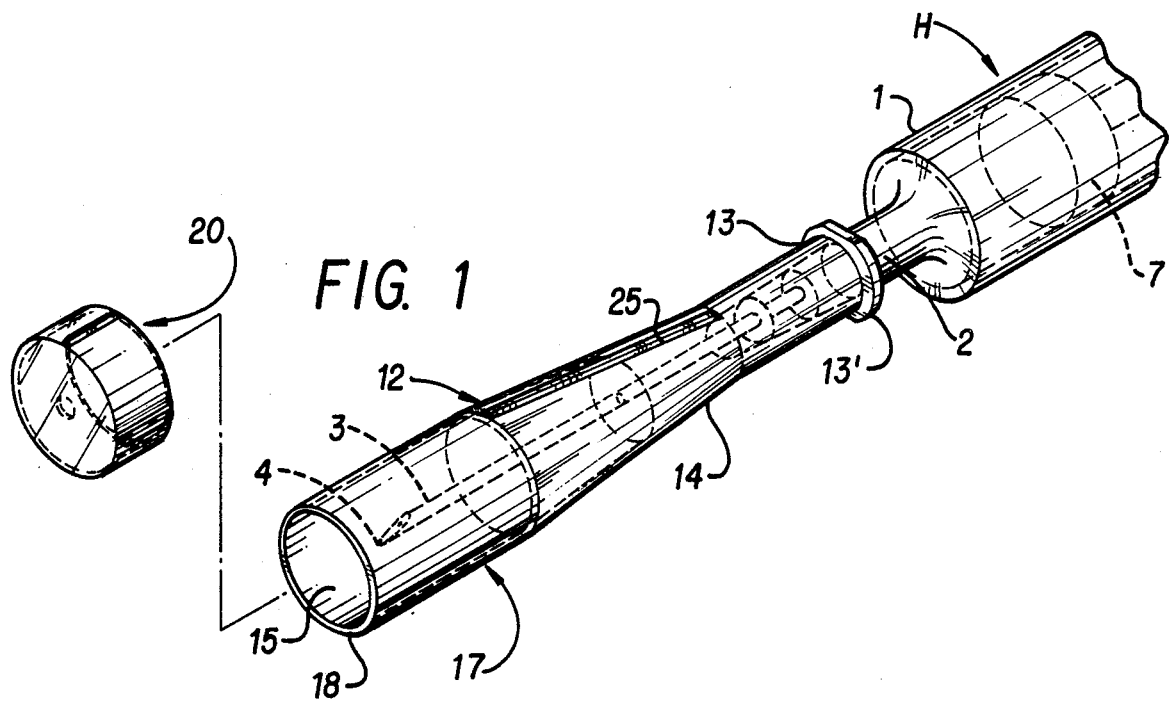
FIG. 1 is a perspective view of the components comprising the medicament injection device.
Figure 2:
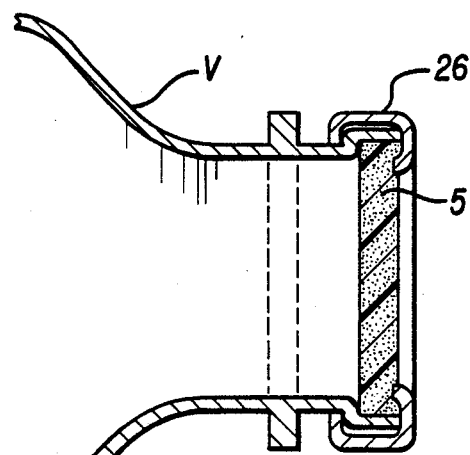
FIG. 2 is a side elevation, partly in section, of a medicament vial usuable with the present invention.

Referring now to the drawings, particularly FIGS. 1 and 2, the present invention will be seen to comprise an assembly or kit of elements as employed in preparation for the administration of intravenous or IV fluids. Included is the primary component namely, a hypodermic syringe H, having a barrel 1 provided with a forward nose 2, to which is affixed a cannula or needle 3 terminating in the conventional distal, sharpened tip 4.

Figure 3:
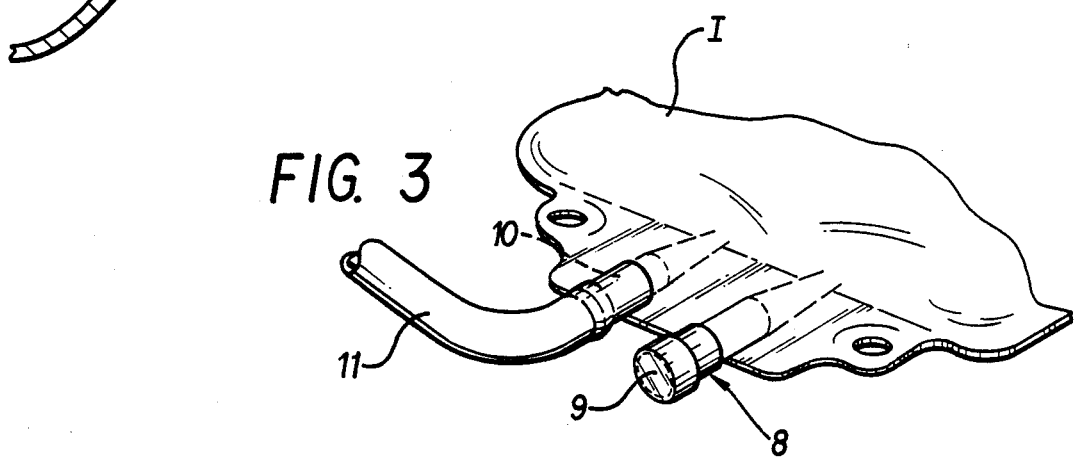
FIG. 3 is a perspective view of an IV bag usable with the present invention.

The usual IV procedure involves insertion of the needle tip 4 through the rupturable membrane 5 inlcuded in the cap 6 of a hand-held medicament vial V, following which the plunger assembly 7 of the syringe H is manipulated to withdraw the prescribed volume of liquid from the vial V. Subsequently, the measured medicament is introduced into the carrier fluid as contained in an IV bag I, such as illustrated in FIG. 3 of the drawings. To facilitate this latter procedure, a suitable input fitting 8 is supplied on the IV bag I and includes a cylindrical end cap 9 likewise having a rupturable seal or membrane through which the needle 3 is inserted to allow discharge of the measured medicament into the IV fluid existing within the bag I. An appropriate output port 10 of any suitable well known construction is included on the bag to allow delivery of the fluid to an IV line 11 for administration to the patient.

During the above manipulations, when using the conventional apparatus, attending personnel are constantaly vulnerable to the dangers of the exposed, sharpened tip 4 of the hypodermic needle 3. Such exposure often results in using personnel sticking or pricking themselves, no matter the degree of precaution being exercised. A prick may be received at any time following removal of the hypodermic syringe H from its sterile packaging and thus may occur before or after withdrawing of the medicament from the vial V or preceding or following the subsequent introduction of the measured medicament into the IV bag I.

The above related danger of needle sticks is of all the more concern in view of the heightened awareness of the transmission of communicable diseases to personnel involved in the direct treatment of patients. Even though treatment personnel regularly wear surgical gloves while administering or withdrawing fluids from patients, such gloves quite obviously offer no protection against needle pricks and accordingly, the following described construction of the present invention will be understood to offer a positive advancement toward precluding attending personnel from receiving needle sticks during the subject procedures.

To overcome the above shortcomings, the assembly of the present invention is provided. As shown most clearly in FIGS. 1 and 4, a shroud or hood member 12 completely surrounds the axial extent of the needle 3 in a manner which isolates its tip 4 from any body contact by using personnel. It will be understood that the syringe utilized with the shroud member is of any conventional construction. The hood 12 includes a rear, attachment base 13 which may be tapered or otherwise configured, to provide a fixed attachment to either the needle hub or nose 2 of the hypodermic syringe H. A rearmost flange 13' radially projects from the attachment base and from FIG. 1 will be seen to include an elongated or irregularly configured periphery to provide an enhanced engagement by a user during the frictional attachment of the shroud member about the syringe nose or needle hub. Extending forwardly of the base 13 is an outwardly tapered section 14 having an inner wall 15 which will be seen to be radially spaced from the shank of the needle 3 to define an inner cavity 16 within the hood 12. Projecting forwardly of the tapered section 14 is a forwardmost, cylindrical section 17 terminating in an end face 18 disposed in a plane well forward of the needle tip 4. The inner wall 15' of the cylindrical section 17 will be understood to form a constant diameter throughout its length for reasons which will become obvious hereinafter.

The internal diameter defined by the inner wall 15' of the cylindrical section 17 and which is designated by the line 19, is no greater than ⅜ inch and is selected to provide a close, sliding fit when applied about the ported fitting of both medicine vials V and IV bags I. Just as important is the disposition of the hood end face 18 significantly forward of the needle tip 4. This tip is preferably recessed from the plane of the shroud end face at least ⅛ inch. In this manner, physical contact between the sharpened tip 4 and any part of a user's anatomy is precluded, even the tip of one's little finger, in view of the radially masked needle.

Figure 4:
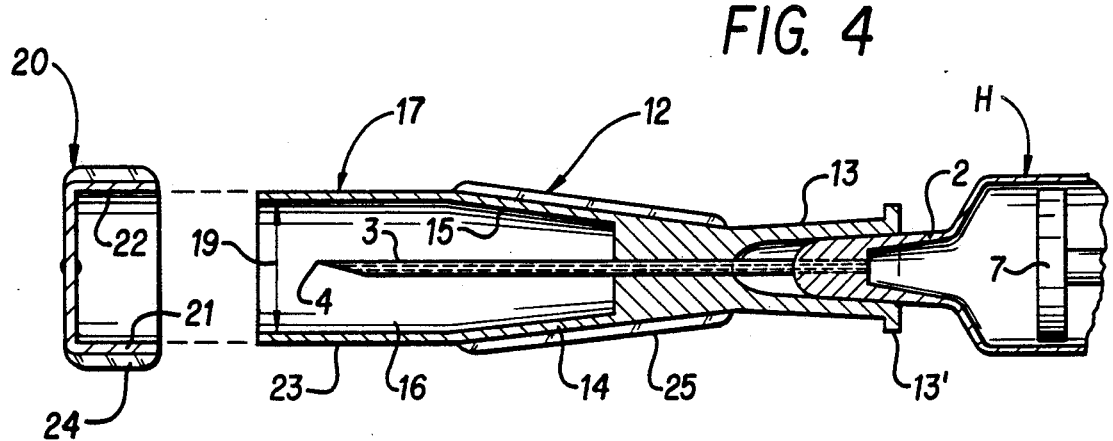
FIG. 4 is a an enlarged vertical sectional view of the device of FIG. 1.

The above shroud assembly 12 may be offered as a separate member, to be affixed to a syringe H at the time of use but preferably, is supplied to the end user already attached as illustrated in FIGS. 1 and 4. In this manner, the completed assembly is provided in a sterile package and at no time is an exposed needle 3 handled by any personnel, thereby insuring the protective feature of the invention, throughout all manipulations of the syringe. As initially delivered to the user, the syringe-hood assembly is completely enclosed by means of an end or safety cap 20 having a skirt 21 provided with an inner wall 22 which presents a friction fit about the external periphery 23 of the hood cylindrical section 17. A plurality of longitudinally extending ribs 24 on the exterior of the cap skirt 21 insure a positive grip as the user grasps the cap to remove it from its frictional engagement about the hood 12. As will be noted, a plurality of similarly configured ribs 25 may be provided on the exterior of the hood tapered section 14 to facilitate the application and/or removal of the hood assembly from the syringe nose 2.

Figure 6:
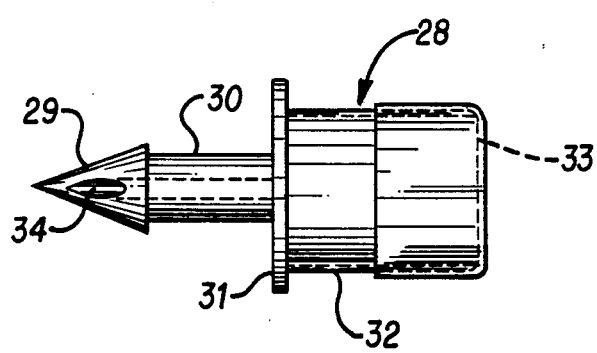
FIG. 6 is side elevation of a piercing device used with the present invention.

In the use of the hooded syringe of the present invention, the safety cap 20 is removed in preparation for withdrawal of a prescribed volume of medicament from a selected vial V. This vial may comprise the type shown in FIG. 2 wherein the cap 26 thereon is provided with the conventional flat diaphragm type stopper 5 intended to be punctured by the conventional exposed hypodermic cannula. With such an arrangement, provision must be made to adapt such a vial stopper to the hooded syringe of the present invention. An appropriate adaptation is provided by means of the piercing or spear device 28 shown in FIG. 6 and which includes a leading, conical point 29 joined to a smaller diameter shank 30 having a radially extending flange or shoulder 31 thereon. Rearwardly of the flange 31 is a stoppered fitting comprising a ported cylindrical member 32 provided with an end seal 33 adapted to be pierced by a cannula. The conical point 29 is provided with a port 34 and which communicates with the hollow interior of the shank 30. The configuration of the ported member 32 is identical to that of the standard ported input fitting 8 on an IV bag I such that the present hooded syringe H may be sequentially attached to both fittings as the medicament is first withdrawn from the vial V and then introduced into the IV bag I. Thus, it will be appreciated that the external periphery of both end caps or seals 9 and 33 provide a close sliding fit within the confines of the hood cylindrical section 17. In this respect, it should be noted that the end face 18 of the hood envelopes the end cap 9 or 33 before the tip 4 punctures the respective membrane and then, after the needle tip has passed therethrough, the syringe is further advanced until the fitting end cap abuts the restricted internal diameter of the hood tapered section 14. At this point, the needle tip 4 is advanced well inwardly of the cap seal or stopper so that manipulation of the syringe plunger 7 will withdraw of expel the medicament. The above mating fit between the shroud 12 and end cap also serves to discourage needle breakage during piercing of the membrane seal. This feature will be understood in view of the central, axial position of the needle 3 within the shroud 12 and the fact that the forward portion of the shroud section 17 initially captively engages the end cap before the needle tip 4 punctures the membrane. Such construction assures a straight, axial movement of the needle as it punctures the very center of the membrane.

Figure 5:
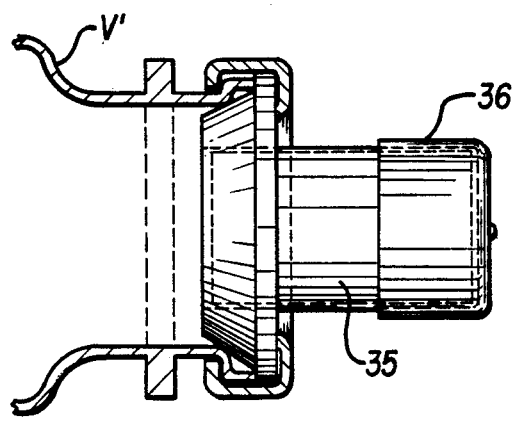
FIG. 5 is a view similar to FIG. 2, or an alternate medicament vial.

FIG. 5 depicts a medicament vial V' as initially supplied with a ported stopper 35 ready to use with the shrouded syringe of present invention. Thus, it follows that the end cap 36 thereof is of identical configuration to the end cap 09 of the piercing device of FIG. 6 as well as that of the input fitting 8 on the IV bag I such that a mating engagement is obtained whenever the hooded syringe H is combined with either stopper construction. Accordingly, it will be appreciated that all three described end caps or fittings 9,33,36 include a rupturable seal and define a cylindrical periphery having a diameter presenting a close, sliding fit with respect to the inner wall 15' of the shroud forward cylindrical section 17.

From the foregoing description it will be seen that an improved construction is provided enabling the safe, no-stick manipulation of a hypodermic syringe when used in combination with both medicament vials of varying construction as well as with IV bags.

It is to be understood that the present invention is not limited to the sole embodiment described above, but encompasses any and all variations falling within the scope of the appended claims.

We claim:

1. A conventional medicament vial end cap membrane piercing device comprising a leasing ported conical point insertable through said membrane closure, said point joined to a smaller diameter shank in communication with a stoppered fitting of a diameter that permits engagement of said fitting by a shrouded syringe.

2. The piercing device of claim 1 wherein said shank has a radially extending flange thereon of a diameter greater than said stoppered fitting.

3. The piercing device of claim 1 wherein said stoppered fitting comprises a ported cylindrical member provided with a membrane end.

4. The piercing device of claim 2 wherein said stoppered fitting compirises a ported cylindrical member provided with a membrane end.

* * * * *